US008691193B2

(12) United States Patent
Rodriguez et al.

(10) Patent No.: US 8,691,193 B2
(45) Date of Patent: Apr. 8, 2014

(54) POLYCONDENSATE, COMPOSITION, TREATMENT PROCESS, AND PREPARATION PROCESS

(75) Inventors: Ivan Rodriguez, Cauffry (FR); Roland Ramin, Paris (FR); Pascal Giustiniani, Levallois Perret (FR); Gerard Malle, Villiers S/Morin (FR); Philippe Ilekti, Maison-Alfort (FR)

(73) Assignee: L'Oreal, Paris (FR)

( * ) Notice: Subject to any disclaimer, the term of this patent is extended or adjusted under 35 U.S.C. 154(b) by 1383 days.

(21) Appl. No.: 11/693,842

(22) Filed: Mar. 30, 2007

(65) Prior Publication Data

US 2008/0069786 A1 Mar. 20, 2008

Related U.S. Application Data

(60) Provisional application No. 60/792,322, filed on Apr. 17, 2006.

(30) Foreign Application Priority Data

Apr. 4, 2006 (FR) ..................................... 06 51190

(51) Int. Cl.
*A61K 8/84* (2006.01)
*A61Q 3/02* (2006.01)

(52) U.S. Cl.
USPC ............................................ 424/61; 523/105

(58) Field of Classification Search
None
See application file for complete search history.

(56) References Cited

U.S. PATENT DOCUMENTS

| 2,915,488 | A | 12/1959 | Kraft et al. | |
| 2002/0037301 | A1* | 3/2002 | De La Poterie | ............... 424/401 |
| 2006/0013788 | A1* | 1/2006 | Filippi | ....................... 424/70.11 |
| 2010/0239509 | A1 | 9/2010 | Chodorowski-Kimmes et al. | |
| 2010/0272660 | A1 | 10/2010 | Malle | |

FOREIGN PATENT DOCUMENTS

| JP | 4-145014 | 5/1992 |
| JP | 8-512348 | 12/1996 |
| JP | 10-306253 | 11/1998 |
| JP | 2002-53433 | 2/2002 |

OTHER PUBLICATIONS

"Soybean Oil", Merck index, 12$^{th}$ edition, edited by Susan Budavari, 1996, monograph 8879, p. 1492.*
Database WPI Week 197910, Derwent Publications Ltd., London, GB; AN 1979-18769B, XP002409236. JP 54 011244, Jan. 27, 1979.
Database WPI Week 197814. Derwent Publications Ltd., London, GB; AN 1978-26140A, XP002409237. JP 53 018742, Feb. 21, 1978.
Database WPI Week 198808. Derwent Publications Ltd., London, GB; AN 1988-052800, XP002409238. JP 63 008318. Jan. 14, 1988.
Database WPI Week 198312. Derwent Publications Ltd., London, GB; AN 1983-28350K, XP002409235. JP 58 023614, Feb. 12, 1983.
U.S. Appl. No. 12/142,413, filed Jun. 19, 2008, Giustiniani, et al.
Notice of reasons for rejection issued Feb. 28, 2012 in JP patent application No. 2007-097695, submitting English translation.

* cited by examiner

*Primary Examiner* — Brian-Yong Kwon
*Assistant Examiner* — Christopher R Lea
(74) *Attorney, Agent, or Firm* — Oblon, Spivak, McClelland, Maier & Neustadt, L.L.P.

(57) ABSTRACT

Polycondensate, composition containing it, especially a nail varnish composition, and process for preparation. The polycondensate may be obtained by reacting:
  a polyol comprising 3 to 6 hydroxyl groups;
  a saturated or unsaturated non-aromatic monocarboxylic acid;
  an aromatic monocarboxylic acid containing 7 to 11 carbon atoms; and
  a saturated or unsaturated, or even aromatic, linear, branched and/or cyclic polycarboxylic acid, comprising at least two carboxylic groups COOH; and/or a cyclic anhydride of such a polycarboxylic acid.

10 Claims, No Drawings

POLYCONDENSATE, COMPOSITION, TREATMENT PROCESS, AND PREPARATION PROCESS

REFERENCE TO PRIOR APPLICATIONS

This application claims priority to U.S. provisional application 60/792,322 filed Apr. 17, 2006, and to French patent application 0651190 filed Apr. 4, 2006, both incorporated herein by reference.

FIELD OF THE INVENTION

The present invention relates to novel polymers of the family of polycondensates of modified alkyd type, and also to their use in compositions, especially cosmetic compositions such as in nail varnishes, to the compositions themselves and to processes for preparing the polycondensates.

Additional advantages and other features of the present invention will be set forth in part in the description that follows and in part will become apparent to those having ordinary skill in the art upon examination of the following or may be learned from the practice of the present invention. The advantages of the present invention may be realized and obtained as particularly pointed out in the appended claims. As will be realized, the present invention is capable of other and different embodiments, and its several details are capable of modifications in various obvious respects, all without departing from the present invention. The description is to be regarded as illustrative in nature, and not as restrictive.

BACKGROUND OF THE INVENTION

Film-forming cosmetic compositions and especially nail varnish compositions should have a certain number of characteristics allowing their application and good durability on the support.

Cosmetic compositions in particular preferably show good applicability and good covering power; good adhesion to the support (surface of the nail, or the hair); a certain amount of flexibility and good strength of the film in order to avoid cracking and chipping in the case of varnishes; the possibility of obtaining a glossy uniform film.

In the field of nail varnishes, the main film-forming material used at the present time is a film-forming resin known as a "primary resin", which is generally nitrocellulose. It is also possible to totally or partly replace it with a polyvinyl resin such as polyvinyl butyrate or alternatively with cellulose acetobutyrate or acetopropionate.

To impart good adhesion, and thus to ensure good durability, secondary resins of different nature are also used, such as arylsulfonamide-formaldehyde or arylsulfonamide-epoxy resins, polyester resins, resins of alkyd type, polyurethane resins, polyester-polyurethane resins, polyether-polyurethane resins, and vinyl and/or acrylic resins, alone or as a mixture.

These secondary resins make it possible to increase the film-forming power of nitrocellulose and improve the gloss and also the adhesion of the films.

Moreover, to adjust the flexibility of the film without weakening its physical strength, plasticizers are used, for instance phthalates or citrates.

In order to improve the durability of the film and its resistance to chipping, various secondary resins, especially of modified alkyd type, have been proposed. Mention may be made in particular of document FR 2 562 793, which describes the use of sucrose benzoate in combination with resins of toluenesulfonamide-formaldehyde type; or document JP-61-246 113, which describes the use of sucrose benzoate in combination with a glycidyl versatate ester-modified alkyd resin. Mention may also be made of WO 2002/243 676, which describes the use of a neopentyl glycol trimellitate adipate polyester resin in combination with alkyl acrylate and methacrylate copolymers.

JP-58-023 614 is also known, which describes the use of modified polyester obtained by condensation of pentaerythritol with cis-4-cyclohexene-1,2-dicarboxylic acid and castor oil fatty acids, followed by reaction with a dioxirane compound of epoxy resin type; or alternatively JP-54-011 244, which describes the use of a modified polyester obtained by condensation of dipentaerythritol with cyclohexane-1,2-dicarboxylic acid and castor oil fatty acids, followed by reaction with a dioxirane compound of epoxy resin type.

However, although these combinations significantly improve the durability, they are still considered insufficient in terms of long durability.

OBJECTS OF THE INVENTION

One object of the present invention is to provide novel polymers that may be used especially as secondary resin and that can thus significantly improve the durability of a film-forming deposit, especially in a nail varnish, while at the same time giving it excellent durability.

To this end, the inventors have discovered novel polycondensates of alkyd type that have the desired properties.

DETAILED DESCRIPTION OF THE PREFERRED EMBODIMENTS

Alkyd resins constitute a particular class of polyesters by being the product of reaction of polyols and of polycarboxylic acids, generally modified with unsaturated fatty acids, such as oleic acid, or with unsaturated oils, for example soybean oil or castor oil, which make it possible to modify their film-forming properties, especially their rate of drying, their hardness, their strength, etc.

Thus, document U.S. Pat. No. 2,915,488 has proposed modified alkyd resins in which some of the fatty acids originating from soybean oil have been replaced with benzoic acid. These novel resins have improved properties in terms of resistance to alkalis and to detergents; films containing them dry faster and are harder. However, no application, and especially no cosmetic or topical application, was envisaged for these resins.

Moreover, it is known that unsaturated fatty acids can undergo autoxidation over time, which is the cause of rancidity phenomena, which may thus lead to problems of storage of compositions comprising these starting materials. Now, it is known that the fatty acids present in soybean oil consist mainly of two unsaturated fatty acids: about 55% of linoleic acid (C18:2) and 286 of oleic acid (C18:1), according to "Surface Coatings Science and Technology", 2nd edition, John Wiley & Sons, pages 104 and 105. The modified resins described in U.S. Pat. No. 2,915,488, which comprise a high proportion of unsaturated fatty acids, therefore still have the drawbacks as regards their use in cosmetics.

After considerable research, the inventors have discovered, surprisingly and unexpectedly, that certain polycondensates with a high content of particular carboxylic acids, including aromatic acids, lead to improved performance in terms of gloss and long durability of the film obtained.

One subject of the present invention is thus a composition comprising, preferably in a cosmetically or pharmaceutically acceptable medium, at least one polycondensate that may be obtained by reacting:

- from 15% to 30% by weight, relative to the total weight of the polycondensate, of at least one polyol comprising 3 to 6 hydroxyl groups;
- from 5% to 40% by weight, relative to the total weight of the polycondensate, of at least one saturated or unsaturated, linear, branched and/or cyclic non-aromatic monocarboxylic acid containing 6 to 32 carbon atoms;
- from 10% to 55% by weight, relative to the total weight of the polycondensate, of at least one aromatic monocarboxylic acid containing 7 to 11 carbon atoms, which is also optionally substituted with 1 to 3 saturated or unsaturated, linear, branched and/or cyclic alkyl radicals containing 1 to 32 carbon atoms;
- from 10% to 25% by weight, relative to the total weight of the polycondensate, of at least one saturated or unsaturated, or even aromatic, linear, branched and/or cyclic polycarboxylic acid, comprising at least two carboxylic groups COOH, especially 2 to 4 COOH groups; and/or a cyclic anhydride of such a polycarboxylic acid.

Another subject of the invention is a polycondensate that may be obtained by reacting:

- from 15% to 30% by weight, relative to the total weight of the polycondensate, of at least one polyol comprising 3 to 6 hydroxyl groups;
- from 5% to 40% by weight, relative to the total weight of the polycondensate, of at least one saturated, linear, branched and/or cyclic non-aromatic monocarboxylic acid containing 6 to 32 carbon atoms;
- from 10% to 55% by weight, relative to the total weight of the polycondensate, of at least one aromatic monocarboxylic acid containing 7 to 11 carbon atoms, which is also optionally substituted with 1 to 3 saturated or unsaturated, linear, branched and/or cyclic alkyl radicals containing 1 to 32 carbon atoms;
- from 10% to 25% by weight, relative to the total weight of the polycondensate, of at least one saturated or unsaturated, or even aromatic, linear, branched and/or cyclic polycarboxylic acid, comprising at least two carboxylic groups COOH, especially 2 to 4 COOH groups; and/or a cyclic anhydride of such a polycarboxylic acid.

Yet another subject of the invention is a process for preparing the polycondensates, which comprises:

- mixing the polyol and the aromatic and non-aromatic monocarboxylic acids,
- heating the mixture under an inert atmosphere, first to the melting point, and then to a temperature of between 150 and 220° C. until the monocarboxylic acids have been totally consumed, then
- optionally cooling the mixture to a temperature of between 90 and 150° C.,
- adding the polycarboxylic acid and/or the cyclic anhydride, and optionally the silicone containing hydroxyl or carboxylic functions, and then
- heating again to a temperature of less than or equal to 220° C.

It has been found that the novel branched polycondensates of alkyd type according to the invention make it possible to formulate long-lasting nail varnish compositions whose covering power and gloss are improved relative to the prior art.

Moreover, these polycondensates are very soluble in solvents of butyl or ethyl acetate type, which facilitates their use in the cosmetic field, especially in nail varnishes.

Another advantage of the polycondensates according to the invention is that they may be readily prepared, in a single synthetic step, without producing waste, and at low cost.

Another advantage lies in the fact that it is easily possible to modify the structure and/or the properties of the polycondensates according to the invention by varying the chemical nature of the various constituents and/or the proportions thereof.

The polycondensates according to the invention are advantageously branched; while not bound by theory it may be thought that this makes it possible to generate a network by interlacing of the polymer chains, and thus to obtain the desired properties, especially in terms of improved durability and in terms of solubility. Specifically, it has been found that linear polycondensates do not make it possible to obtain an appreciable improvement in the durability of the composition, and that polycondensates of dendrimer type, whose chains are regular, do not have optimum solubility.

The polycondensates according to the invention are polycondensates of alkyd type, and are thus able to be obtained by esterification/polycondensation, according to the methods known to those skilled in the art, from the constituents described below.

One of the constituents for the preparation of the polycondensates according to the invention is a compound comprising 3 to 6 hydroxyl groups (polyol), especially 3 to 4 hydroxyl groups. A mixture of such polyols may be used.

The polyol may especially be a linear, branched and/or cyclic, saturated or unsaturated carbon-based and especially hydrocarbon-based compound, containing 3 to 18 carbon atoms, especially 3 to 12 or even 4 to 10 carbon atoms, and 3 to 6 hydroxyl (OH) groups, and also possibly comprising one or more oxygen atoms intercalated in the chain (ether function).

The polyol is preferably a linear or branched saturated hydrocarbon-based compound containing 3 to 18 carbon atoms, especially 3 to 12 or even 4 to 10 carbon atoms, and 3 to 6 hydroxyl (OH) groups.

It may be chosen, alone or as a mixture, for example from:
- triols such as 1,2,6-hexanetriol, trimethylolethane, trimethylolpropane or glycerol;
- tetraols such as pentaerythritol (tetramethylolmethane), erythritol, diglycerol or ditrimethylolpropane;
- pentols such as xylitol;
- hexyls such as sorbitol and mannitol; or alternatively dipentaerythritol or triglycerol.

Preferably, the polyol is chosen from glycerol, pentaerythritol and sorbitol, and mixtures thereof, and better still is pentaerythritol.

The polyol, or the polyol mixture, preferably represents 15% to 30% by weight, especially 16% to 28% by weight and better still 18% to 25% by weight relative to the total weight of the final polycondensate.

Another constituent for the preparation of the polycondensates according to the invention is a saturated or unsaturated, linear, branched and/or cyclic non-aromatic monocarboxylic acid containing 6 to 32 carbon atoms, especially 8 to 28 carbon atoms and better still 10 to 20 or even 12 to 18 carbon atoms. A mixture of such non-aromatic monocarboxylic acids may obviously be used.

The term "non-aromatic monocarboxylic acid" means a compound of formula RCOOH, in which R is a saturated or unsaturated, linear, branched and/or cyclic hydrocarbon-based radical containing 5 to 31 carbon atoms, especially 7 to 27 carbon atoms and better still 9 to 19 carbon atoms or even 11 to 17 carbon atoms.

Preferably, the radical R is saturated. Better still, the radical R is linear or branched, and is preferably of C5-C31.

Among the non-aromatic monocarboxylic acids that may be used, particular mention may be made, alone or as a mixture, of:
- saturated monocarboxylic acids such as caproic acid, caprylic acid, isoheptanoic acid, 4-ethylpentanoic acid, 2-ethylhexanoic acid, 4,5-dimethylhexanoic acid, 2-heptylhexanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentane-carboxylic acid, cyclopentaneacetic acid, 3-cyclo-pentylpropionic acid, cyclohexanecarboxylic acid, cyclohexylacetic acid or 4-cyclohexylbutyric acid;
- unsaturated but non-aromatic monocarboxylic acids, such as caproleic acid, undecylenic acid, dodecylenic acid, myristoleic acid, palmitoleic acid, oleic acid, elaidic acid, gondoic acid or erucic acid.

2-Ethylhexanoic acid, isooctanoic acid, lauric acid, palmitic acid or isostearic acid, and mixtures thereof, and better still isostearic acid alone, may preferably be used.

The non-aromatic monocarboxylic acid, or the mixture of the acids, preferably represents 5% to 40% by weight, especially 8% to 38% by weight and better still 10% to 35% by weight relative to the total weight of the final polycondensate.

Another constituent for the preparation of the polycondensates according to the invention is an aromatic monocarboxylic acid containing 7 to 11 carbon atoms, also optionally substituted with 1 to 3 saturated or unsaturated, linear, branched and/or cyclic alkyl radicals containing 1 to 32 carbon atoms, especially 2 to 12 or even 3 to 8 carbon atoms.

A mixture of such aromatic monocarboxylic acids may obviously be used.

The term "aromatic monocarboxylic acid" means a compound of formula R'COOH, in which R' is an aromatic hydrocarbon-based radical containing 6 to 10 carbon atoms, and in particular benzoic and naphthoic radicals. The radical R' may also be substituted with 1 to 3 saturated or unsaturated, linear, branched and/or cyclic alkyl radicals containing 1 to 32 carbon atoms, especially 2 to 12 or even 3 to 8 carbon atoms; and especially chosen from methyl, ethyl, propyl, isopropyl, butyl, isobutyl, tert-butyl, pentyl, isopentyl, neopentyl, cyclopentyl, hexyl, cyclohexyl, heptyl, isoheptyl, octyl and isooctyl.

Among the aromatic monocarboxylic acids that may be used, particular mention may be made, alone or as a mixture, of benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid.

Preferably, benzoic acid, o-toluic acid, m-toluic acid or 1-naphthoic acid, alone or as mixtures, and better still benzoic acid alone, may be used.

The aromatic monocarboxylic acid, or the mixture of the acids, preferably represents 10% to 55% by weight, especially 20% to 52% by weight, or even 22% to 52% by weight and better still 25% to 50% by weight relative to the total weight of the final polycondensate.

Another constituent for the preparation of the polycondensates according to the invention is a saturated or unsaturated, or even aromatic, linear, branched and/or cyclic polycarboxylic acid, comprising at least 2 carboxylic groups COOH and especially 2 to 4 COOH groups; and/or a cyclic anhydride of such a polycarboxylic acid. A mixture of such polycarboxylic acids and/or anhydrides may obviously be used.

The polycarboxylic acid may especially be chosen from linear, branched and/or cyclic, saturated or unsaturated, or even aromatic, polycarboxylic acids containing 2 to 20 carbon atoms, especially 3 to 18 and better still 4 to 12 carbon atoms, or even 4 to 10 carbon atoms; the acid comprises at least two carboxylic groups COOH and preferably from 2 to 4 COOH groups.

Preferably, the polycarboxylic acid is a saturated linear aliphatic acid and contains 2 to 20 carbon atoms, especially 3 to 18 carbon atoms or even 4 to 12 carbon atoms; or alternatively is aromatic and contains 8 to 12 carbon atoms. It preferably comprises 2 to 4 COOH groups.

The cyclic anhydride of such a polycarboxylic acid may especially correspond to one of the following formulae:

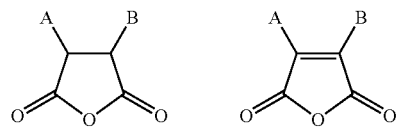

in which the groups A and B are, independently of each other:
- a hydrogen atom;
- a saturated or unsaturated, linear, branched and/or cyclic aliphatic, or alternatively aromatic, carbon-based radical; containing 1 to 16 carbon atoms, especially 2 to 10 carbon atoms or even 4 to 8 carbon atoms, especially methyl or ethyl;
- or alternatively A and B, taken together, form a saturated or unsaturated, or even aromatic, ring containing in total 5 to 7 and especially 6 carbon atoms.

Preferably, A and B represent a hydrogen atom or together form an aromatic ring containing in total 6 carbon atoms.

Among the polycarboxylic acids or anhydrides thereof that may be used, particular mention may be made, alone or as a mixture, of:
- dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid or maleic acid;
- tricarboxylic acids such as cyclohexanetricarboxylic acid, trimellitic acid, 1,2,3-benzenetricarboxylic acid or 1,3,5-benzenetricarboxylic acid;
- tetracarboxylic acids such as butanetetracarboxylic acid and pyromellitic acid;
- cyclic anhydrides of these acids and especially phthalic anhydride, trimellitic anhydride, maleic anhydride and succinic anhydride.

Phthalic anhydride and/or isophthalic acid, and better still isophthalic acid alone, may preferably be used.

The polycarboxylic acid and/or the cyclic anhydride thereof preferably represents 10% to 25% by weight, especially 11% to 22% by weight and better still 12% to 20% by weight relative to the total weight of the final polycondensate.

The polycondensate according to the invention may also comprise a silicone containing hydroxyl (OH) and/or carboxylic (COOH) functions.

It may comprise 1 to 3 hydroxyl and/or carboxylic functions, and preferably comprises two hydroxyl functions or two carboxylic functions.

These functions may be located at the end of a chain or in the chain, but advantageously at the end of the chain.

Silicones with a weight-average molecular mass (Mw) of between 300 and 20 000, especially 400 and 10 000 or even 800 and 4000, are preferably used.

This silicone may be of the formula:

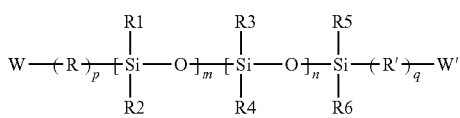

in which:

W and W' are, independently of each other, OH or COOH; preferably, W=W';

p and q are, independently of each other, equal to 0 or 1;

R and R' are, independently of each other, a saturated or unsaturated, or even aromatic, linear, branched and/or cyclic carbon-based and especially hydrocarbon-based divalent radical; containing 1 to 12 carbon atoms and especially 2 to 8 carbon atoms, and optionally also comprising one or more heteroatoms chosen from O, S and N, especially 0 (ether);

R and/or R' may especially be of formula $-(CH_2)_a-$ with a=1-12, and especially methylene, ethylene, propylene or phenylene;

or alternatively of formula $-[(CH_2)_xO]_z-$ with x=1, 2 or 3 and z=1-10; in particular x=2 or 3 and z=1-4; and better still x=3 and z=1;

R1 to R6 are, independently of each other, a linear, branched and/or cyclic, saturated or unsaturated, or even aromatic, carbon-based radical containing 1 to 20 carbon atoms and especially 2 to 12 carbon atoms; preferably, R1 to R6 are saturated or aromatic, and may be chosen especially from alkyl radicals, in particular methyl, ethyl, propyl, isopropyl, butyl, pentyl, hexyl, octyl, decyl, dodecyl and octadecyl radicals, cycloalkyl radicals, in particular the cyclohexyl radical, aryl radicals, especially phenyl and naphthyl, arylalkyl radicals, especially benzyl and phenylethyl, and also tolyl and xylyl radicals;

m and n are, independently of each other, integers between 1 and 140, and are such that the weight-average molecular mass (Mw) of the silicone is between 300 and 20 000, especially between 400 and 10 000 or even between 800 and 4000.

Mention may be made especially of α,ω-diol or α,ω-dicarboxylic polyalkylsiloxanes and especially α,ω-diol polydimethylsiloxanes and α,ω-dicarboxylic poly-dimethylsiloxanes; α,ω-diol or α,ω-dicarboxylic poly-arylsiloxanes and especially α,ω-diol or α,ω-dicarboxylic polyphenylsiloxanes; polyarylsiloxanes containing silanol functions such as polyphenylsiloxane; polyalkylsiloxanes containing silanol functions such as polydimethylsiloxane; polyaryl/alkylsiloxanes containing silanol functions such as polyphenyl/methylsiloxane or polyphenyl/propylsiloxane.

α,ω-Diol polydimethylsiloxanes with a weight-average molecular mass (Mw) of between 400 and 10 000 or even between 500 and 5000 and especially between 800 and 4000 will be used most particularly.

When it is present, the silicone may preferably represent 0.1% to 15% by weight, especially 1% to 10% by weight or even 2% to 8% by weight relative to the weight of the polycondensate.

In one preferred embodiment of the invention, the aromatic monocarboxylic acid is present in a molar amount greater than or equal to that of the non-aromatic monocarboxylic acid; in particular, the ratio between the number of moles of aromatic monocarboxylic acid and the number of moles of non-aromatic monocarboxylic acid is preferably between 1.2 and 8, in particular between 1.3 and 7.8 or even between 1.4 and 7.5 and better still between 1.9 and 7.

It has been found that this especially makes it possible to obtain a polymer that is advantageously soluble in the short esters (such as butyl or ethyl acetate) generally used for formulating cosmetic compositions of nail varnish type; moreover, the film obtained is sufficiently rigid for use in nail varnish formulations.

Preferably, the polycondensate according to the invention may be obtained by reacting:

at least one polyol chosen, alone or as a mixture, from 1,2,6-hexanetriol, trimethylolethane, trimethylolpropane, glycerol; pentaerythritol, erythritol, diglycerol, ditrimethylolpropane; xylitol, sorbitol, mannitol, dipentaerythritol and/or triglycerol; preferably present in an amount of 15% to 30% by weight, especially 16% to 28% by weight and better still 18% to 25% by weight, relative to the total weight of the final polycondensate;

at least one non-aromatic monocarboxylic acid chosen, alone or as a mixture, from caproic acid, caprylic acid, isoheptanoic acid, 4-ethylpentanoic acid, 2-ethylhexanoic acid, 4,5-dimethylhexanoic acid, 2-heptylhexanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid or 4-cyclohexylbutyric acid; preferably present in an amount of 5% to 40% by weight, especially 8% to 38% by weight and better still 10% to 35% by weight relative to the total weight of the final polycondensate;

at least one aromatic monocarboxylic acid chosen, alone or as a mixture, from benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid; preferably present in an amount of 10% to 55% by weight, especially 20% to 52% by weight and better still 25% to 50% by weight relative to the total weight of the final polycondensate; and at least one polycarboxylic acid or an anhydride thereof, chosen, alone or as a mixture, from decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid or maleic acid; cyclohexanetricarboxylic acid, trimellitic acid, 1,2,3-benzenetricarboxylic acid, 1,3,5-benzenetricarboxylic acid; butanetetracarboxylic acid, pyromellitic acid, phthalic anhydride, trimellitic anhydride, maleic anhydride and succinic anhydride;

preferably present in an amount of 10% to 25% by weight, especially 11% to 22% by weight and better still 12% to 20% by weight relative to the total weight of the final polycondensate.

Preferentially, the polycondensate according to the invention may be obtained by reacting:
- at least one polyol chosen, alone or as a mixture, from glycerol, pentaerythritol and sorbitol, and mixtures thereof, and better still pentaerythritol alone; present in an amount of 15% to 30% by weight, especially 16% to 28% by weight and better still 18% to 25% by weight relative to the total weight of the final polycondensate;
- at least one non-aromatic monocarboxylic acid chosen, alone or as a mixture, from 2-ethylhexanoic acid, isooctanoic acid, lauric acid, palmitic acid and isostearic acid, and mixtures thereof, and better still isostearic acid alone; present in an amount of 5% to 40% by weight, especially 8% to 38% by weight and better still 10% to 35% by weight relative to the total weight of the final polycondensate;
- at least one aromatic monocarboxylic acid chosen, alone or as a mixture, from benzoic acid, o-toluic acid, m-toluic acid and 1-naphthoic acid, and better still benzoic acid alone; present in an amount of 10% to 55% by weight, especially 20% to 52% by weight and better still 25% to 50% by weight relative to the total weight of the final polycondensate; and
- at least one polycarboxylic acid or an anhydride thereof, chosen, alone or as a mixture, from phthalic anhydride and isophthalic acid, and better still isophthalic acid alone; present in an amount of 10% to 25% by weight, especially 11% to 22% by weight and better still 12% to 20% by weight relative to the total weight of the final polycondensate.

Preferably, the polycondensate according to the invention has:
- an acid number, expressed in mg of potassium hydroxide per g of polycondensate, of greater than or equal to 8; especially between 8 and 40 and better still between 10 and 30; and/or
- a hydroxyl number, expressed in mg of potassium hydroxide per g of polycondensate, of greater than or equal to 30; especially between 30 and 100 and better still between 40 and 90.

These acid and hydroxyl numbers may be readily determined by a person skilled in the art via the usual analytical methods.

Preferably, the polycondensate according to the invention has a viscosity, measured at 110° C., of between 75 and 6000 mPa·s, especially between 80 and 5500 mPa·s, or even between 90 and 5000 mPa·s and better still between 200 and 4800 mPa·s. This viscosity is measured in the manner described before the examples.

Moreover, the polycondensate is advantageously soluble in short esters, containing in total 3 to 8 carbon atoms, especially C1-C6 carboxylic acid acetates, and in particular butyl acetate and/or ethyl acetate.

The term "soluble" means that the polymer forms a clear solution in butyl acetate or ethyl acetate, in a proportion of at least 50% by weight, at 25° C.; preferably, the polymer according to the invention is soluble in a proportion of at least 70% by weight in butyl acetate or ethyl acetate.

Preferably, the solution of the polymer according to the invention in butyl acetate or ethyl acetate, at 25° C., at a concentration of 70% by weight, has a viscosity of between 100 and 1500 mPa·s and especially between 120 and 900 mPa·s. The measuring method is given before the examples.

The polycondensate according to the invention may be prepared via the esterification/polycondensation processes usually used by those skilled in the art. By way of illustration, a general preparation process consists in:
- mixing the polyol and the aromatic and non-aromatic monocarboxylic acids,
- heating the mixture under an inert atmosphere, first to the melting point (generally 100-130° C.) and then to a temperature of between 150 and 220° C. until the monocarboxylic acids have been totally consumed (achieved when the acid number is less than or equal to 1), preferably while gradually distilling off the water formed, then optionally cooling the mixture to a temperature of between 90 and 150° C.,
- adding the polycarboxylic acid and/or the cyclic anhydride, and optionally the silicone containing hydroxyl or carboxylic functions, in a single portion or sequentially, and then
- heating again to a temperature of less than or equal to 220° C., especially between 170 and 220° C., preferably while continuing to remove the water formed, until the required characteristics in terms of acid number, viscosity, hydroxyl number and solubility are obtained.

It is possible to add conventional esterification catalysts, for example of sulfonic acid type (especially in a weight concentration of between 1% and 10%) or of titanate type (especially in a weight concentration of between 5 and 100 ppm).

It is also possible to perform the reaction, totally or partly, in an inert solvent such as xylene and/or under reduced pressure, to facilitate the removal of the water.

Advantageously, neither catalyst nor solvent is used.

The preparation process may also comprise a step of adding at least one antioxidant to the reaction medium, especially in a weight concentration of between 0.01% and 1% relative to the total weight of monomers, so as to limit the possible degradation associated with prolonged heating.

The antioxidant may be of primary type or secondary type, and may be chosen from hindered phenols, aromatic secondary amines, organophosphorus compounds, sulfur compounds, lactones and acrylic bisphenols; and mixtures thereof.

Among the antioxidants that are particularly preferred, particular mention may be made especially of BHT, BHA, TBHQ, 1,3,5-trimethyl-2,4,6-tris(3,5-di-tert-butyl-4-hydroxybenzyl)benzene, octadecyl 3,5-di-tert-butyl-4-hydroxycinnamate, methanetetrakis[methylene-3-(3,5-di-tert-butyl-4-hydroxyphenyl) propionate], octadecyl 3-(3,5-di-tert-butyl-4-hydroxyphenyl)propionate 2,5-di-tert-butylhydroquinone, 2,2-methylbis(4-methyl-6-tert-butylphenol), 2,2-methylenebis(4-ethyl-6-tert-butylphenol), 4,4-butylidenebis(6-tert-butyl-m-cresol), N,N-hexamethylenebis(3,5-di-tert-butyl-4-hydroxyhydrocinnamamide), pentaerythritoltetrakis(3-(3,5-di-tert-butyl-4-hydroxyphenyl) propionate), especially the product sold by Ciba under the name Irganox 1010; octadecyl 3-(3,5-di-tert-butyl-4-hydroxyphenyl)propionate, especially the product sold by Ciba under the name Irganox 1076; 1,3,5-tris(3,5-di-tert-butyl-4-hydroxybenzyl)-1,3,5-triazine-2,4,6-(1H,3H,5H)-trione, especially the product sold by Mayzo of Norcross, Ga. under name BNX 3114; di(stearyl)pentaerythritol diphosphite, tris (2,4-di-tert-butylphenyl) phosphite, especially the product sold by Ciba under the name Irgafos 168; dilauryl thiodipropionate, especially the product sold by Ciba under the name Irganox PS800; bis(2,4-di-tert-butyl)pentaerythritol diphosphite, especially the product sold by Ciba under the name Irgafos 126; bis(2,4-bis)[2-phenylpropan-2-yl]phenyl)pentaerythritol diphosphite, triphenyl phosphite, (2,4-di-tert-butylphenyl)pentaerythritol diphosphite, especially the product sold by GE Specialty Chemicals under the name Ultranox 626; tris(nonylphenyl) phosphite, especially the product sold by Ciba under the name Irgafos TNPP; the 1:1 mixture of N,N-hexamethylenebis(3,5-di-tert-butyl-4-hydroxyhydrocinnamamide) and of tris(2,4-di-tert-butylphenyl) phosphate, especially the product sold by Ciba under the name Irganox B1171; tetrakis(2,4-di-tert-butylphenyl) phosphite, especially the product sold by Ciba under the name Irgafos P-EPQ; distearyl thiodipropionate, especially the product sold by Ciba under the name Irganox PS802; 2,4-bis(octylthiomethyl)-o-cresol, especially the product sold by Ciba under the name Irganox 1520; 4,6-bis(dodecylthiomethyl)-o-cresol, especially the product sold by Ciba under the name Irganox 1726.

The polycondensates according to the invention may be used very advantageously in a composition, especially a cosmetic or pharmaceutical composition, which moreover comprises a physiologically acceptable and especially a cosmetically or pharmaceutically acceptable medium, i.e. a medium that is compatible with cutaneous tissue, for instance facial or bodily skin, and keratin materials such as the hair, the eyelashes, the eyebrows and the nails.

The amount of polycondensate present in the compositions depends on the type of composition and the desired properties, and may vary within a very wide range generally of between 0.1% and 70% by weight and more, preferably between 2% at 50% by weight, especially between 31 and 35% by weight, or even between 5% and 20% by weight and better still between 6% and 18% by weight relative to the weight of the final cosmetic or pharmaceutical composition.

The composition may then comprise, according to the intended application, the constituents common to this type of composition.

The composition according to the invention may advantageously comprise a solvent medium for the polymers according to the invention, which may comprise at least one compound chosen from water, alcohols, polyols, ketones, esters, ethers, alkanes, aldehydes, carbon-based oils, silicone oils and fluorosilicone oils, and mixtures thereof; preferably, an organic solvent medium comprising an organic solvent or a mixture of organic solvents.

Preferably, the physiologically acceptable medium of the composition according to the invention may comprise at least one organic solvent chosen from:
  ketones that are liquid at room temperature (25° C.), such as methyl ethyl ketone, methyl isobutyl ketone, diisobutyl ketone, isophorone, cyclohexanone or acetone;
  alcohols that are liquid at room temperature, such as ethanol, isopropanol, diacetone alcohol, 2-butoxyethanol or cyclohexanol;
  propylene glycol ethers that are liquid at room temperature, such as propylene glycol monomethyl ether, propylene glycol monomethyl ether acetate or dipropylene glycol mono-n-butyl ether;
  cyclic ethers such as γ-butyrolactone;
  short-chain esters (containing from 3 to 8 carbon atoms in total) such as ethyl acetate, methyl acetate, propyl acetate, isopropyl acetate, n-butyl acetate, isopentyl acetate, methoxypropyl acetate or butyl lactate;
  ethers that are liquid at room temperature, such as diethyl ether, dimethyl ether or dichlorodiethyl ether;
  alkanes, especially of C5-C12, that are liquid at room temperature, such as decane, heptane, dodecane, isododecane or cyclohexane;
  aldehydes that are liquid at room temperature, such as benzaldehyde or acetaldehyde;
  and mixtures thereof.

Preferably, the solvent is chosen from short-chain esters containing from 3 to 8 carbon atoms, such as ethyl acetate, methyl acetate, propyl acetate, isopropyl acetate, n-butyl acetate, isopentyl acetate, methoxypropyl acetate or butyl lactate; alcohols that are liquid at room temperature, such as ethanol, isopropanol, diacetone alcohol, 2-butoxyethanol or cyclohexanol; and mixtures thereof.

The organic solvent medium, alone or as a mixture, may represent for example from 10% to 95% by weight, preferably from 15% to 80% by weight and better still from 20% to 60% by weight relative to the total weight of the composition.

The composition according to the invention may also comprise carbon-based, hydrocarbon-based, fluoro and/or silicone oils of mineral, animal, plant or synthetic origin, alone or as a mixture, provided that they form a uniform and stable mixture and that they are compatible with the intended use. Among the oils that may be present in the composition according to the invention, particular mention may be made, alone or as a mixture, of hydrocarbon-based oils such as liquid paraffin or liquid petroleum jelly; perhydrosqualene; arara oil; sweet almond oil, beauty-leaf oil, palm oil, castor oil, avocado oil, jojoba oil, olive oil or cereal germ oil; lanolic acid, oleic acid, lauric acid or stearic acid esters; alcohols such as oleyl alcohol, linoleyl alcohol, linolenyl alcohol, isostearyl alcohol or octyldodecanol. Mention may also be made of silicone oils such as optionally phenylated PDMSs, such as phenyl trimethicones. Mention may also be made of volatile oils, such as cyclotetradimethylsiloxane, cyclopentadimethylsiloxane, cyclohexadimethylsiloxane, methylhexyldimethylsiloxane, hexamethyldisiloxane or isoparaffins.

The oils, alone or as a mixture, may represent for example 0.01% to 20% by weight, preferably 0.05% to 10% by weight and better still 0.1% to 8% by weight relative to the total weight of the composition.

The composition according to the invention may advantageously comprise a film-forming polymer.

According to the present invention, the term "film-forming polymer" means a polymer that is capable, by itself or in the presence of an auxiliary film-forming agent, of forming a continuous film that adheres to a support and especially to keratin materials.

Among the film-forming polymers that may be used in the composition of the present invention, particular mention may be made of synthetic polymers, of free-radical type or of polycondensate type, and polymers of natural origin, and mixtures thereof. They may be chosen in particular from cellulose-based polymers such as nitrocellulose, cellulose acetate, cellulose acetobutyrate, cellulose acetopropionate and ethylcellulose, or alternatively polyurethanes, acrylic polymers, vinyl polymers, polyvinyl butyrals, alkyd resins, resins derived from aldehyde condensation products such as arylsulfonamide-formaldehyde resins, for instance toluenesulfonamide-formaldehyde resin, arylsulfonamide-epoxy resins or ethyltosylamide resins.

The film-forming polymer may be present in the composition according to the invention in a content ranging from 1% to 70% by weight, preferably ranging from 2% to 60% by weight and better still from 5% to 45% by weight relative to the total weight of the composition.

To improve the film-forming properties of the composition, especially when it is a nail varnish, an auxiliary film-forming agent may be added thereto.

Such an auxiliary film-forming agent may be chosen from any compound known to those skilled in the art as being capable of fulfilling the desired function, and may be chosen especially from plasticizers and coalescers. In particular, mention may be made, alone or as a mixture, of common plasticizers and coalescers, such as:

- glycols and derivatives thereof, such as diethylene glycol ethyl ether, diethylene glycol methyl ether, diethylene glycol butyl ether or diethylene glycol hexyl ether, ethylene glycol ethyl ether, ethylene glycol butyl ether or ethylene glycol hexyl ether;
- polyethylene glycols, polypropylene glycols, polyethylene glycol-polypropylene glycol copolymers and mixtures thereof, especially polypropylene glycols of high molecular weight having, for example, a molecular mass ranging from 500 to 15 000;
- glycol esters;
- propylene glycol derivatives and in particular propylene glycol phenyl ether, propylene glycol diacetate, dipropylene glycol ethyl ether, tripropylene glycol methyl ether, diethylene glycol methyl ether and propylene glycol butyl ether;
- acid esters, especially carboxylic acid esters, such as citrates, phthalates, adipates, carbonates, tartrates, phosphates and sebacates; esters derived from the reaction of a monocarboxylic acid of formula $R_{11}COOH$ with a diol of formula $HOR_{12}OH$ with $R_{11}$ and $R_{12}$, which may be identical or different, representing a linear, branched or cyclic, saturated or unsaturated hydrocarbon-based chain preferably containing from 3 to 15 carbon atoms and optionally containing one or more heteroatoms such as N, O or S;
- oxyethylenated derivatives such as oxyethylenated oils, especially plant oils such as castor oil;
- dimethicone copolyols, especially containing propyl polyoxypropylene groups; and
- mixtures thereof.

The composition may also comprise a thickener, which may for example be chosen in particular from:

- silicas, especially hydrophobic silicas, such as those described in document EP-A-898 960 and sold, for example, under the references Aerosil R812® by the company Degussa, Cab-O—Sil TS-530®, Cab-O-Sil TS-610® Cab-O-Sil TS-720® by the company Cabot, Aerosil R972® and Aerosil R974® by the company Degussa;
- clays such as montmorillonite, modified clays such as bentones, for example stearalkonium hectorite and stearalkonium bentonite,
- polysaccharide alkyl ethers (especially in which the alkyl group contains from 1 to 24, preferably from 1 to 10, better still from 1 to 6 and more especially from 1 to 3 carbon atoms) such as those described in document EP-A-898 958.

The amount of thickener in the composition according to the invention may range for example from 0.01% to 15% by weight, preferably from 0.1% to 12% and better still from 0.5% to 10% by weight relative to the total weight of the composition.

The composition according to the invention may also comprise a secondary resin in addition to the polycondensate according to the invention and the film-forming polymer, which may be chosen from arylsulfonamide-formaldehyde or arylsulfonamide-epoxy resins, polyester resins, resins of alkyd type, polyurethane resins, polyester-polyurethane resins, polyether-polyurethane resins and vinyl and/or acrylic resins, alone or as a mixture. This additional secondary resin may be present in a proportion of from 1% to 20% by weight, preferably from 2% to 15% by weight and better still from 3% to 10% by weight relative to the total weight of the composition.

The composition according to the invention may also comprise at least one wax of plant, animal, mineral or synthetic, or even silicone, origin. Particular mention may be made in particular, alone or as a mixture, of hydrocarbon-based waxes such as beeswax; carnauba wax, candelilla wax, ouricury wax, Japan wax, cork fibre wax or sugarcane wax; paraffin wax, lignite wax; microcrystalline waxes; lanolin wax; montan wax; ozokerites; polyethylene waxes; the waxes obtained by Fischer-Tropsch synthesis; hydrogenated oils, fatty esters and glycerides that are solid at 25° C. Silicone waxes may also be used, among which particular mention may be made of alkyl or alkoxy polymethylsiloxanes and/or polymethylsiloxane esters.

The amount of wax in the composition according to the invention may range for example from 0.01% to 159 by weight, preferably from 0.1% to 10% and better still from 0.5% to 15% by weight relative to the total weight of the composition.

The composition according to the invention may also comprise one or more dyestuffs chosen from water-soluble dyes and pulverulent dyestuffs, for instance pigments, fillers, nacres and flakes, and/or liposoluble or water-soluble dyes.

The dyestuffs, which are especially pulverulent, may be present in the composition in a content ranging for example from 0.01% to 50% by weight, preferably from 0.1% to 40% by weight or even 1% to 30% by weight relative to the weight of the composition.

The term "pigments" should be understood as meaning white or coloured, mineral or organic particles of any form, which are insoluble in the physiological medium, and which are intended to colour the composition.

The term "nacres" should be understood as meaning iridescent particles of any form, especially produced by certain molluscs in their shell, or else synthesized.

The pigments may be white or coloured, mineral and/or organic, and interference or non-interference pigments. Among the mineral pigments that may be mentioned are titanium dioxide, optionally surface-treated, zirconium oxide or cerium oxide, and also zinc oxide, iron oxide or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment of the abovementioned type and also nacreous pigments based on bismuth oxychloride.

The fillers may be mineral or organic, and lamellar or spherical. Mention may be made of talc, mica, silica, kaolin, Nylon powders, poly-β-alanine powders and polyethylene powders, Teflon, lauroyllysine, starch, boron nitride, tetrafluoroethylene polymer powders, hollow microspheres such as Expancel (Nobel Industrie), Polytrap (Dow Corning) and silicone resin microbeads (for example Tospearls from Toshiba), precipitated calcium carbonate, magnesium carbonate, magnesium hydrocarbonate, hydroxyapatite, hollow silica microspheres (Silica Beads from Maprecos), glass or ceramic microcapsules, and metal soaps derived from organic carboxylic acids containing from 8 to 22 carbon atoms and preferably from 12 to 18 carbon atoms, for example zinc, magnesium or lithium stearate, zinc laurate or magnesium myristate.

The liposoluble dyes are, for example, Sudan red, DC Red 17, DC Green 6, β-carotene, soybean oil, Sudan brown, DC Yellow 11, DC Violet 2, DC Orange 5 or quinoline yellow; they may represent 0.01% to 20% and better still from 0.1% to 6% of the weight of the composition.

The water-soluble dyes are, for example, beetroot juice or methylene blue, and may represent 0.01% to 6% of the total weight of the composition.

The composition may also comprise other ingredients commonly used in cosmetic compositions. Such ingredients may be chosen from antioxidants, fragrances, essential oils, preserving agents, cosmetic active agents, moisturizers, vitamins, ceramides, sunscreens, surfactants, spreading agents, wetting agents, dispersants, antifoams, neutralizers and stabilizers, and mixtures thereof.

Needless to say, a person skilled in the art will take care to select this or these additional compound(s), and/or the amount thereof, such that the advantageous properties of the composition for the use according to the invention are not, or are not substantially, adversely affected by the envisaged addition.

The compositions according to the invention may be in any form including those that are acceptable and common for a cosmetic or pharmaceutical composition.

They may thus be in the form of a suspension, a dispersion, especially of oil in water by means of vesicles; an organic or oily solution that is optionally thickened or even gelled; an oil-in-water, water-in-oil or multiple emulsion; a gel or a mousse; an oily or emulsified gel; a dispersion of vesicles, especially lipid vesicles; a two-phase or multiphase lotion; a spray; a lotion, a cream, a salve, a soft paste, an ointment, a cast or moulded solid, especially in the form of a stick or a dish, or a compacted solid.

Preferably, the compositions according to the invention are in the form of an organic solution.

A person skilled in the art can choose the appropriate galenical form, and also the method for preparing it, on the basis of this disclosure and his general knowledge, taking into account firstly the nature of the constituents used, especially their solubility in the support, and secondly the intended use of the composition.

The cosmetic composition according to the invention may be in the form of a care and/or makeup product for bodily or facial skin, the lips, the eyelashes, the eyebrows, the hair, the scalp or the nails; an antisun or self-tanning product; a hair-care product.

The compositions in accordance with the invention may be used for caring for or making up keratin materials such as the hair, the skin, the eyelashes, the eyebrows, the nails, the lips or the scalp and more particularly the nails.

Specifically, the polymers according to the invention find a particularly advantageous application in the field of nail makeup. The compositions of the invention are advantageously in the form of nail varnish, especially comprising the polycondensates according to the invention used as secondary resin, in combination with a main resin that may be chosen from the film-forming polymers described above.

Preferentially, the cosmetic compositions, in particular nail varnishes, according to the invention comprise:
  0.1% to 50% by weight, preferably between 2% and 35% by weight, especially between 5% and 20% by weight and better still between 6% and 18% by weight, relative to the weight of the cosmetic composition, of polycondensate according to the invention, alone or as a mixture;
  1% to 70% by weight, preferably 2% to 60% by weight and better still 5% to 45% by weight, relative to the total weight of the cosmetic composition, of film-forming polymer, chosen especially from cellulose-based polymers such as nitrocellulose, cellulose acetate, cellulose acetobutyrate, cellulose acetopropionate or ethylcellulose; polyurethanes, acrylic polymers, vinyl polymers, polyvinyl butyrals, alkyd resins, resins derived from the products of condensation of aldehyde, such as arylsulfonamide-formaldehyde resins, for instance toluene-sulfonamide-formaldehyde resin, arylsulfonamide-epoxy resins or ethyltosylamide resins; polymers of natural origin; and mixtures thereof;
  10% to 95% by weight, preferably 15% to 80% by weight and better still 20% to 60% by weight, relative to the total weight of the cosmetic composition, of organic solvent, chosen especially from ketones that are liquid at room temperature; alcohols that are liquid at room temperature; propylene glycol ethers that are liquid at room temperature; cyclic ethers; short-chain esters (containing from 3 to 8 carbon atoms in total); ethers that are liquid at room temperature; alkanes that are liquid at room temperature; aldehydes that are liquid at room temperature; and mixtures thereof;
  optionally at least one dyestuff, which may be present in the composition in a content of from 0.01% to 50% by weight, preferably from 0.1% to 40% by weight or even from 1% to 30% by weight relative to the weight of the composition.

A subject of the invention is also a cosmetic process for treating keratin materials, especially bodily or facial skin, the nails, the hair and/or the eyelashes, comprising the application to the materials of a cosmetic composition as defined above.

This process according to the invention especially allows the nails to be made up, by applying a nail varnish composition according to the invention.

The invention is illustrated in greater detail in the examples that follow.

Method for Measuring the Viscosity a/ The viscosity at 110° C. of the polymer is measured using a cone-plate viscometer of Brookfield CAP 1000+ type.

The appropriate cone-plate is determined by a person skilled in the art, on the basis of his knowledge; especially:
  between 50 and 500 mPa·s, a 02 cone may be used
  between 500 and 1000 mPa·s: cone 03
  between 1000 and 4000 mPa·s: cone 05
  between 4000 and 10 000 mPa·s: cone 06 b/ The viscosity at 25° C. of the solution of the polymer at 70% in butyl acetate is measured using a Brookfield DV-I viscometer, at 30 rpm using an S62 spindle.

EXAMPLE 1

Synthesis of pentaerythrityl benzoate/isophthalate/isostearate 227.5 g of benzoic acid, 72.8 g of isostearic acid and 118.3 g of pentaerythritol are placed in a reactor equipped with a mechanical stirrer, an argon inlet and a distillation system, and the mixture is then heated gradually, under a gentle stream of argon, to 110-130° C. to obtain a homogeneous solution. The temperature is then raised gradually to 180° C. and maintained for about 2 hours. The temperature is again raised to 220° C. and maintained until an acid number of less than or equal to 1 is obtained, which takes about 18 hours. The mixture is cooled to a temperature of between 100 and 130°

C., 91 g of isophthalic acid are then introduced and the mixture is again heated gradually to 220° C. over about 11 hours.

430 g of pentaerythrityl benzoate/isophthalate/isostearate polycondensate are thus obtained in the form of a thick oil that solidifies at room temperature.

The polycondensate has the following characteristics:
acid number=12.7
hydroxyl number=49
$\eta_{110°\ C.}$=25.4 poises (i.e. 2540 mPa·s)
ratio between the number of moles of aromatic monocarboxylic acid and the number of moles of non-aromatic monocarboxylic acid: 7.28.

420 g of polycondensate obtained above are taken and heated to 100-120° C., 180 g of butyl acetate are run in slowly with stirring, and the mixture is then clarified by filtration while hot through a No. 2 sinter funnel.

After cooling to room temperature, 600 g of solution of polycondensate at 70' in butyl acetate are obtained, in the form of a pale yellow viscous liquid with a viscosity at 25° C. of about 800 centipoises (mPa·s).

EXAMPLE 2

Synthesis of pentaerythrityl benzoate/isophthalate/laurate/PDMS 150 g of benzoic acid, 165 g of lauric acid and 110 g of pentaerythritol are placed in a reactor equipped with a mechanical stirrer, an argon inlet and a distillation system, and the mixture is then heated gradually, under a gentle stream of argon, to 110-130° C. to obtain a homogeneous solution. The temperature is then gradually increased to 180° C. and maintained for about 2 hours. The temperature is again raised to 220° C. and maintained until an acid number of less than or equal to 1 is obtained, which takes about 15 hours. The mixture is cooled to a temperature of between 100 and 130° C., 90 g of isophthalic acid and 50 g of α,ω-diol silicone X22-160AS from Shin-Etsu are then introduced and the mixture is again gradually heated to 220° C. over about 11 hours.

510 g of pentaerythrityl benzoate/isophthalate/laurate/PDMS polycondensate are thus obtained in the form of a thick oil that solidifies at room temperature.

The polycondensate has the following characteristics:
acid number=28.7
hydroxyl number=85
$\eta_{110°\ C.}$=2.1 poises (i.e. 210 mPa·s)
ratio between the number of moles of aromatic monocarboxylic acid and the number of moles of non-aromatic monocarboxylic acid: 1.49.

500 g of polycondensate obtained above are taken and heated to 70° C., 215 g of ethyl acetate are run in slowly with stirring, and the mixture is then clarified by filtration while hot through a No. 2 sinter funnel. After cooling to room temperature, 705 g of solution of polycondensate at 70% in ethyl acetate are obtained, in the form of a pale yellow viscous liquid with a viscosity at 25° C. of about 165 centipoises (mPa·s).

EXAMPLE 3

Synthesis of pentaerythrityl benzoate/isophthalate/laurate 165 g of benzoic acid, 160 g of lauric acid and 120 g of pentaerythritol are placed in a reactor equipped with a mechanical stirrer, an argon inlet and a distillation system, and the mixture is then heated gradually, under a gentle stream of argon, to 110-130° C. to obtain a homogeneous solution. The temperature is then raised gradually to 180° C. and maintained for about 2 hours. The temperature is again raised to 220° C. and maintained until an acid number of less than or equal to 1 is obtained, which takes about 15 hours. The mixture is cooled to a temperature of between 100 and 130° C., 100 g of isophthalic acid are then introduced and the mixture is again heated gradually to 220° C. over about 12 hours.

510 g of pentaerythrityl benzoate/isophthalate/laurate polycondensate are thus obtained in the form of a thick oil that solidifies at room temperature.

The polycondensate has the following characteristics:
acid number=20.4
hydroxyl number=66
$\eta_{110°\ C.}$=4.7 poises (i.e. 470 mPa·s)
ratio between the number of moles of aromatic monocarboxylic acid and the number of moles of non-aromatic monocarboxylic acid: 1.69.

500 g of polycondensate obtained above are taken and heated to 70° C., 215 g of ethyl acetate are run in slowly with stirring, and the mixture is then clarified by filtration while hot through a No. 2 sinter funnel. After cooling to room temperature, 700 g of solution of polycondensate at 70% in ethyl acetate are obtained, in the form of a pale yellow viscous liquid with a viscosity at 25° C. of about 310 centipoises (mPa·s).

EXAMPLE 4

Synthesis of Pentaerythrityl benzoate/phthalate/laurate 185 g of benzoic acid, 174 g of lauric acid and 114.6 g of pentaerythritol are placed in a reactor equipped with a mechanical stirrer, an argon inlet and a distillation system, and the mixture is then heated gradually, under a gentle stream of argon, to 110-130° C. to obtain a homogeneous solution. The temperature is then raised gradually to 180° C. and maintained for about 2 hours. The temperature is again raised to 220° C. and maintained until an acid number of less than or equal to 1 is obtained, which takes about 18 hours. The mixture is cooled to a temperature of between 100 and 130° C., 80 g of phthalic acid are then introduced and the mixture is again heated gradually to 220° C. over about 8 hours. 15 g of pentaerythritol are added and the mixture is maintained at 220° C. for 8 hours.

512 g of pentaerythrityl benzoate/phthalate/laurate polycondensate are thus obtained in the form of a thick oil that solidifies at room temperature.

The polycondensate has the following characteristics:
acid number=13.0
hydroxyl number=60
$\eta_{110°\ C.}$=0.9 poises (i.e. 90 mPa·s)
ratio between the number of moles of aromatic monocarboxylic acid and the number of moles of non-aromatic monocarboxylic acid: 1.74.

EXAMPLE 5

A cherry-red coloured nail varnish was prepared using the following composition:

| | |
|---|---|
| Nitrocellulose at 30% in isopropanol | 14 g |
| Alkyd resin Beckosol ODE-230-70E at 70% in ethyl acetate | 5.2 g |
| Solution of the polymer of Example 1 at 70% in butyl acetate | 10.8 g |
| Isopropanol | 3.6 g |
| Ethyl acetate | 23 g |
| Butyl acetate | 33.5 g |
| Tributyl acetyl citrate | 3.4 g |

| | |
|---|---|
| N-Ethyl-o,p-toluenesulfonamide | 3.4 g |
| Citric acid | 0.05 g |
| Modified hectorite | 1.3 g |
| Pigments (lakes) | 1.3 g |

The varnish applies easily and forms a very glossy film that is very resistant to external attack.

EXAMPLE 6

A cherry-red coloured nail varnish was prepared using the following composition:

| | |
|---|---|
| Nitrocellulose at 30% in isopropanol | 14 g |
| Alkyd resin Beckosol ODE-230-70E at 70% in ethyl acetate | 5.2 g |
| Solution of the polymer of Example 2 at 70% in ethyl acetate | 11.2 g |
| Isopropanol | 3.6 g |
| Ethyl acetate | 19.5 g |
| Butyl acetate | 36.5 g |
| Tributyl acetyl citrate | 3.4 g |
| N-Ethyl-o,p-toluenesulfonamide | 3.4 g |
| Citric acid | 0.05 g |
| Modified hectorite | 1.3 g |
| Pigments (lakes) | 1.3 g |

The varnish applies easily and forms a very glossy film that is very resistant to external attack.

EXAMPLE 7

A coloured nail varnish was prepared using the following composition (% by weight):

| | |
|---|---|
| Nitrocellulose at 30% in isopropanol | 14% |
| Solution of the polymer of Example 1 at 70% in butyl acetate | 17% |
| Isopropanol | 3.6% |
| Ethyl acetate | 23% |
| Butyl acetate | qsp 100% |
| Tributyl acetyl citrate | 3.2% |
| N-Ethyl-o,p-toluenesulfonamide | 3.6% |
| Citric acid | 0.05% |
| Modified hectorite | 1.3% |
| Pigments (lakes) | 1.3% |

The varnish applies easily and forms a very glossy film that is very resistant to external attack.

Preferred embodiments of the invention described and enabled herein include the embodiments appended hereto, which make up a part of this specification, and the following preferred embodiments, numbered 18-66, where embodiments 18 and 21 refer back to the following embodiment "A":

A composition comprising, preferably in a cosmetically or pharmaceutically acceptable medium, at least one polycondensate that may be or is obtained by reacting:
from 15% to 30% by weight, relative to the total weight of the polycondensate, of at least one polyol comprising 3 to 6 hydroxyl groups;
from 5% to 40% by weight, relative to the total weight of the polycondensate, of at least one saturated or unsaturated, linear, branched and/or cyclic non-aromatic monocarboxylic acid containing 6 to 32 carbon atoms;
from 100- to 550 by weight, relative to the total weight of the polycondensate, of at least one aromatic monocarboxylic acid containing 7 to 11 carbon atoms, which is also optionally substituted with 1 to 3 saturated or unsaturated, linear, branched and/or cyclic alkyl radicals containing 1 to 32 carbon atoms;
from 10% to 25% by weight, relative to the total weight of the polycondensate, of at least one saturated or unsaturated, or even aromatic, linear, branched and/or cyclic polycarboxylic acid, comprising at least two carboxylic groups COOH, especially 2 to 4 COOH groups; and/or a cyclic anhydride of such a polycarboxylic acid.

18. Composition according to the preceding embodiment, in which the polycarboxylic acid is chosen from linear, branched and/or cyclic, saturated or unsaturated, or even aromatic polycarboxylic acids containing 2 to 20 carbon atoms, especially 3 to 18 and better still 4 to 12 carbon atoms, or even 4 to 10 carbon atoms; the acid comprising at least two carboxylic groups COOH and preferably from 2 to 4 COOH groups.

19. Composition according to Embodiment 18, in which the polycarboxylic acid is a saturated linear aliphatic acid and contains 2 to 20 carbon atoms, especially 3 to 18 carbon atoms, or even 4 to 12 carbon atoms.

20. Composition according to Embodiment 18, in which the polycarboxylic acid is aromatic and contains 8 to 12 carbon atoms.

21. Composition according to one of Embodiment A, in which the cyclic anhydride corresponds to one of the following formulae:

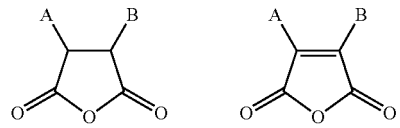

in which the groups A and B are, independently of each other:
a hydrogen atom;
a saturated or unsaturated, linear, branched and/or cyclic aliphatic, or alternatively aromatic, carbon-based radical; containing 1 to 16 carbon atoms, especially 2 to 10 carbon atoms or even 4 to 8 carbon atoms, especially methyl or ethyl;
or alternatively A and B, taken together, form a saturated or unsaturated, or even aromatic, ring containing in total 5 to 7 and especially 6 carbon atoms.

22. Composition according to Embodiment 21, in which A and B represent a hydrogen atom or together form an aromatic ring containing in total 6 carbon atoms.

23. Composition according to one of the preceding embodiments, in which the polycarboxylic acid or the anhydride thereof is chosen, alone or as a mixture, from:
dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid or maleic acid;
tricarboxylic acids such as cyclohexanetricarboxylic acid, trimellitic acid, 1,2,3-benzenetricarboxylic acid or 1,3,5-benzenetricarboxylic acid;
tetracarboxylic acids such as butanetetracarboxylic acid and pyromellitic acid;

cyclic anhydrides of these acids and especially phthalic anhydride, trimellitic anhydride, maleic anhydride and succinic anhydride.

24. Composition according to one of the preceding embodiments, in which the polycarboxylic acid or the anhydride thereof is chosen from phthalic anhydride and/or isophthalic acid, and better still isophthalic acid alone.

25. Composition according to one of the preceding embodiments, in which the polycarboxylic acid and/or the cyclic anhydride thereof represents 11% to 22% by weight and better still 12% to 20% by weight relative to the total weight of the polycondensate.

26. Composition according to one of the preceding embodiments, in which the polycondensate also comprises at least one silicone containing hydroxyl (OH) and/or carboxylic (COOH) functions.

27. Composition according to Embodiment 26, in which the silicone has a weight-average molecular mass (Mw) of between 300 and 20 000, especially 400 and 10 000 or even 800 and 4000.

28. Composition according to either of Embodiments 26 and 27, in which the silicone is of the formula:

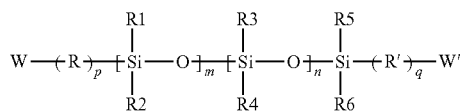

in which:
W and W' are, independently of each other, OH or COOH; preferably, W=W';
p and q are, independently of each other, equal to 0 or 1;
R and R' are, independently of each other, a saturated or unsaturated, or even aromatic, linear, branched and/or cyclic carbon-based and especially hydrocarbon-based divalent radical; containing 1 to 12 carbon atoms and especially 2 to 8 carbon atoms, and optionally also comprising one or more heteroatoms chosen from O, S and N, especially 0 (ether);
R and/or R' may especially be of formula —(CH$_2$)$_a$— with a=1-12, and especially methylene, ethylene, propylene or phenylene;
or alternatively of formula —[(CH$_2$)$_x$O]$_z$— with x=1, 2 or 3 and z=1-10; in particular x=2 or 3 and z=1-4; and better still x=3 and z=1;
R1 to R6 are, independently of each other, a linear, branched and/or cyclic, saturated or unsaturated, or even aromatic, carbon-based radical containing 1 to 20 carbon atoms and especially 2 to 12 carbon atoms; preferably, R1 to R6 are saturated or aromatic, and may be chosen especially from alkyl radicals, in particular methyl, ethyl, propyl, isopropyl, butyl, pentyl, hexyl, octyl, decyl, dodecyl and octadecyl radicals, cycloalkyl radicals, in particular the cyclohexyl radical, aryl radicals, especially phenyl and naphthyl, arylalkyl radicals, especially benzyl and phenylethyl, and also tolyl and xylyl radicals;
m and n are, independently of each other, integers between 1 and 140, and are such that the weight-average molecular mass (Mw) of the silicone is between 300 and 20 000, especially between 400 and 10 000 or even between 800 and 4000.

29. Composition according to one of Embodiments 26 to 28, in which the silicone is chosen, alone or as a mixture, from α,ω-diol or α,ω-dicarboxylic polyalkylsiloxanes and especially α,ω-diol polydimethylsiloxanes and α,ω-dicarboxylic polydimethylsiloxanes; α,ω-diol or α,ω-dicarboxylic polyarylsiloxanes and especially α,ω-diol or α,ω-dicarboxylic polyphenylsiloxanes; polyarylsiloxane; polyalkylsiloxanes containing silanol functions such as polyphenylsiloxane; polyalkylsiloxanes containing silanol functions such as polydimethylsiloxane; polyaryl/alkylsiloxanes containing silanol functions such as polyphenyl/methylsiloxane or polyphenyl/propylsiloxane.

30. Composition according to one of Embodiments 26 to 29, in which the silicone is chosen from α,ω-diol polydimethylsiloxanes with a weight-average molecular mass (Mw) of between 400 and 10 000, or even between 500 and 5000 and especially between 800 and 4000.

31. Composition according to one of Embodiments 26 to 30, in which the silicone represents 0.1% to 15% by weight, especially 1% to 10% by weight or even 2% to 8% by weight relative to the total weight of the polycondensate.

32. Composition according to one of the preceding embodiments, in which the ratio between the number of moles of aromatic monocarboxylic acid and the number of moles of non-aromatic monocarboxylic acid is between 1.2 and 8, in particular between 1.3 and 7.8, or even between 1.4 and 7.5 and better still between 1.9 and 7.

33. Composition according to one of the preceding embodiments, in which the polycondensate may be obtained by reacting:
at least one polyol chosen, alone or as a mixture, from 1,2,6-hexanetriol, trimethylolethane, trimethylolpropane, glycerol; pentaerythritol, erythritol, diglycerol, ditrimethylolpropane; xylitol, sorbitol, mannitol, dipentaerythritol and/or triglycerol; preferably present in an amount of 15% to 30% by weight, especially 16% to 28% by weight and better still 18% to 25% by weight, relative to the total weight of the final polycondensate;
at least one non-aromatic monocarboxylic acid chosen, alone or as a mixture, from caproic acid, caprylic acid, isoheptanoic acid, 4-ethylpentanoic acid, 2-ethylhexanoic acid, 4,5-dimethylhexanoic acid, 2-heptylhexanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid or 4-cyclohexylbutyric acid; preferably present in an amount of 5% to 40% by weight, especially 8% to 38% by weight and better still 10% to 35% by weight relative to the total weight of the final polycondensate;
at least one aromatic monocarboxylic acid chosen, alone or as a mixture, from benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid; preferably present in an amount of 10% to 55% by weight, especially 20% to 52% by weight and better still 25% to 50% by weight relative to the total weight of the final polycondensate; and
at least one polycarboxylic acid or an anhydride thereof, chosen, alone or as a mixture, from decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid or maleic acid; cyclohexanetricarboxylic acid, trimellitic acid, 1,2,3-benzenetricarboxylic acid, 1,3,5-benzenetricarboxylic acid; butanetetracarboxylic acid, pyromellitic acid, phthalic anhydride, trimellitic anhydride, maleic anhydride and succinic anhydride; preferably present in an amount of 10% to 25% by weight, especially 11% to 22% by weight and better still 12% to 20% by weight relative to the total weight of the final polycondensate.

34. Composition according to one of the preceding embodiments, in which the polycondensate may be obtained by reacting:
at least one polyol chosen, alone or as a mixture, from glycerol, pentaerythritol and sorbitol, and mixtures thereof, and better still pentaerythritol alone; present in an amount of 15% to 30% by weight, especially 16% to 28% by weight and better still 18% to 25% by weight relative to the total weight of the final polycondensate;
at least one non-aromatic monocarboxylic acid chosen, alone or as a mixture, from 2-ethylhexanoic acid, isooctanoic acid, lauric acid, palmitic acid and isostearic acid, and mixtures thereof, and better still isostearic acid alone; present in an amount of 5% to 40% by weight, especially 8% to 38% by weight and better still 10% to 35% by weight relative to the total weight of the final polycondensate;
at least one aromatic monocarboxylic acid chosen, alone or as a mixture, from benzoic acid, o-toluic acid, m-toluic acid and 1-naphthoic acid, and better still benzoic acid alone; present in an amount of 10% to 55% by weight, especially 20% to 52% by weight and better still 25% to 50% by weight relative to the total weight of the final polycondensate; and
at least one polycarboxylic acid or an anhydride thereof, chosen, alone or as a mixture, from phthalic anhydride and isophthalic acid, and better still isophthalic acid alone; present in an amount of 10% to 25% by weight, especially 11% to 22% by weight and better still 12% to 20% by weight relative to the total weight of the final polycondensate.

35. Composition according to one of the preceding embodiments, in which the polycondensate has at least one of the following characteristics:
an acid number, expressed in mg of potassium hydroxide per g of polycondensate, of greater than or equal to 8; especially between 8 and 40 and better still between 10 and 30; and/or
a hydroxyl number, expressed in mg of potassium hydroxide per g of polycondensate, of greater than or equal to 30; especially between 30 and 100 and better still between 40 and 90,
a viscosity, measured at 110° C., of between 75 and 6000 mPa·s, especially between 80 and 5500 mPa·s, or even between 90 and 5000 mPa·s and better still between 200 and 4800 mPa·s;
a solubility in butyl acetate or ethyl acetate, in a proportion of at least 50% by weight, at 25° C.;
a viscosity of a solution of the polymer in butyl acetate or ethyl acetate, at 25° C., at a concentration of 70% by weight, of between 100 and 1500 mPa·s and especially between 120 and 900 mPa·s.

36. Composition according to one of the preceding embodiments, in which the polycondensate is present in an amount of between 0.1% and 70% by weight, preferably between 2% and 50% by weight, especially between 3% and 35% by weight, or even between 5% and 20% by weight, and better still between 6% and 18% by weight, relative to the weight of the final cosmetic or pharmaceutical composition.

37. Composition according to one of the preceding embodiments, in which the cosmetically or pharmaceutically acceptable medium comprises at least one compound chosen from water, alcohols, polyols, ketones, esters, ethers, alkanes, aldehydes, carbon-based oils, silicone oils and fluorosilicone oils, and mixtures thereof.

38. Composition according to one of the preceding embodiments, in which the cosmetically or pharmaceutically acceptable medium comprises at least one organic solvent chosen from:
ketones that are liquid at room temperature (25° C.), such as methyl ethyl ketone, methyl isobutyl ketone, diisobutyl ketone, isophorone, cyclohexanone or acetone;
alcohols that are liquid at room temperature, such as ethanol, isopropanol, diacetone alcohol, 2-butoxyethanol or cyclohexanol;
propylene glycol ethers that are liquid at room temperature, such as propylene glycol monomethyl ether, propylene glycol monomethyl ether acetate or dipropylene glycol mono-n-butyl ether;
cyclic ethers such as γ-butyrolactone;
short-chain esters (containing from 3 to 8 carbon atoms in total) such as ethyl acetate, methyl acetate, propyl acetate, isopropyl acetate, n-butyl acetate, isopentyl acetate, methoxypropyl acetate or butyl lactate;
ethers that are liquid at room temperature, such as diethyl ether, dimethyl ether or dichlorodiethyl ether;
alkanes, especially of C5-C12, that are liquid at room temperature, such as decane, heptane, dodecane, isododecane or cyclohexane;
aldehydes that are liquid at room temperature, such as benzaldehyde or acetaldehyde;
and mixtures thereof.

39. Composition according to one of the preceding embodiments, in which the cosmetically or pharmaceutically acceptable medium comprises at least one solvent chosen from short-chain esters containing from 3 to 8 carbon atoms, such as ethyl acetate, methyl acetate, propyl acetate, isopropyl acetate, n-butyl acetate, isopentyl acetate, methoxypropyl acetate, butyl lactate; alcohols that are liquid at room temperature, such as ethanol, isopropanol, diacetone alcohol, 2-butoxyethanol or cyclohexanol; and mixtures thereof.

40. Composition according to one of the preceding embodiments, in which the cosmetically or pharmaceutically acceptable medium comprises at least one constituent chosen from carbon-based, hydrocarbon-based, fluoro and/or silicone oils of mineral, animal, plant or synthetic origin; film-forming polymers; auxiliary film-forming agents; thickeners; secondary resins; waxes of plant, animal, mineral or synthetic origin, or even silicone waxes; dyestuffs; antioxidants, fragrances, essential oils, preserving agents, cosmetic active agents, moisturizers, vitamins, ceramides, sunscreens, surfactants, spreading agents, wetting agents, dispersants, antifoams, neutralizers and stabilizers, and mixtures thereof.

41. Composition according to one of the preceding embodiments, comprising:
0.1% to 50% by weight, preferably between 2% and 35% by weight, especially between 5% and 20% by weight and better still between 6% and 18% by weight, relative to the weight of the cosmetic composition, of polycondensate according to one of the preceding embodiments, alone or as a mixture;
1% to 70% by weight, preferably 2% to 60% by weight and better still 5% to 45% by weight, relative to the total weight of the cosmetic composition, of film-forming polymer, chosen especially from cellulose-based polymers such as nitrocellulose, cellulose acetate, cellulose acetobutyrate, cellulose acetopropionate or ethylcellulose; polyurethanes, acrylic polymers, vinyl polymers, polyvinyl butyrals, alkyd resins, resins derived from the products of condensation of aldehyde, such as arylsulfonamide-formaldehyde resins, for instance toluene sulfonamide-formaldehyde resin, arylsulfonamide-epoxy resins or ethyltosylamide resins; polymers of natural origin; and mixtures thereof;

10% to 95% by weight, preferably 15% to 80% by weight and better still 20% to 60% by weight, relative to the total weight of the cosmetic composition, of organic solvent, chosen especially from ketones that are liquid at room temperature; alcohols that are liquid at room temperature; propylene glycol ethers that are liquid at room temperature; cyclic ethers; short-chain esters (containing from 3 to 8 carbon atoms in total); ethers that are liquid at room temperature; alkanes that are liquid at room temperature; aldehydes that are liquid at room temperature; and mixtures thereof;

optionally at least one dyestuff, which may be present in the composition in a content of from 0.01% to 50% by weight, preferably from 0.1% to 40% by weight or even from 1% to 30% by weight relative to the weight of the composition.

42. Composition according to one of the preceding embodiments, which is in the form of a care and/or makeup product for bodily or facial skin, the lips, the eyelashes, the eyebrows, the hair, the scalp or the nails; an antisun or self-tanning product; a haircare product.

43. Composition according to one of the preceding embodiments, which is in the form of a nail varnish.

44. Cosmetic process for treating keratin materials, especially bodily or facial skin, the nails, the hair and/or the eyelashes, comprising the application to the materials of a cosmetic composition as defined herein.

45. Cosmetic process for making up the nails, comprising the application to the nails of a cosmetic composition as defined herein.

46. Polycondensate that may be obtained by reacting:
from 15% to 30% by weight, relative to the total weight of the polycondensate, of at least one polyol comprising 3 to 6 hydroxyl groups;
from 5% to 40% by weight, relative to the total weight of the polycondensate, of at least one saturated, linear, branched and/or cyclic non-aromatic monocarboxylic acid containing 6 to 32 carbon atoms;
from 10% to 55% by weight, relative to the total weight of the polycondensate, of at least one aromatic monocarboxylic acid containing 7 to 11 carbon atoms, which is also optionally substituted with 1 to 3 saturated or unsaturated, linear, branched and/or cyclic alkyl radicals containing 1 to 32 carbon atoms;
from 10% to 25% by weight, relative to the total weight of the polycondensate, of at least one saturated or unsaturated, or even aromatic, linear, branched and/or cyclic polycarboxylic acid, comprising at least two carboxylic groups COOH, especially 2 to 4 COOH groups; and/or a cyclic anhydride of such a polycarboxylic acid.

47. Polycondensate according to Embodiment 46, in which the polyol is a linear, branched and/or cyclic, saturated or unsaturated carbon-based and especially hydrocarbon-based compound, containing 3 to 18 carbon atoms, especially 3 to 12 or even 4 to 10 carbon atoms, and 3 to 6 hydroxyl (OH) groups, and also possibly comprising one or more oxygen atoms intercalated in the chain (ether function).

48. Polycondensate according to either of Embodiments 46 and 47, in which the polyol is chosen, alone or as a mixture, from:
triols such as 1,2,6-hexanetriol, trimethylolethane, trimethylolpropane or glycerol;
tetraols such as pentaerythritol, erythritol, diglycerol or ditrimethylolpropane;
pentols such as xylitol;
hexyls such as sorbitol and mannitol; or alternatively dipentaerythritol or triglycerol.

49. Polycondensate according to one of Embodiments 46 to 48, in which the polyol, or the polyol mixture, represents 16% to 28% by weight and better still 18% to 25% by weight relative to the total weight of the polycondensate.

50. Polycondensate according to one of Embodiments 46 to 49, in which the saturated non-aromatic monocarboxylic acid is of formula RCOOH, in which R is a saturated, linear, branched and/or cyclic hydrocarbon-based radical containing 5 to 31 carbon atoms, especially 7 to 27 carbon atoms and better still 9 to 19 carbon atoms, or even 11 to 17 carbon atoms.

51. Polycondensate according to one of Embodiments 46 to 50, in which the non-aromatic monocarboxylic acid is chosen, alone or as a mixture, from caproic acid, caprylic acid, isoheptanoic acid, 4-ethylpentanoic acid, 2-ethylhexanoic acid, 4,5-dimethylhexanoic acid, 2-heptylheptanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid or 4-cyclohexylbutyric acid.

52. Polycondensate according to one of Embodiments 46 to 51, in which the non-aromatic monocarboxylic acid, or the mixture of the acids, represents 8% to 38% by weight and better still 10% to 35% by weight relative to the total weight of the polycondensate.

53. Polycondensate according to one of Embodiments 46 to 52, in which the aromatic monocarboxylic acid is of formula R'COOH, in which R' is an aromatic hydrocarbon-based radical containing 6 to 10 carbon atoms, and in particular benzoic and naphthoic radicals; the radical R' may also be substituted with 1 to 3 saturated or unsaturated, linear, branched and/or cyclic alkyl radicals containing 1 to 32 carbon atoms, especially 2 to 12 or even 3 to 8 carbon atoms; and especially chosen from methyl, ethyl, propyl, isopropyl, butyl, isobutyl, tert-butyl, pentyl, isopentyl, neopentyl, cyclopentyl, hexyl, cyclohexyl, heptyl, isoheptyl, octyl and isooctyl.

54. Polycondensate according to one of Embodiments 46 to 53, in which the aromatic monocarboxylic acid is chosen, alone or as a mixture, from benzoic acid, o-toluic acid, m-toluic acid, p-toluic acid, 1-naphthoic acid, 2-naphthoic acid, 4-tert-butylbenzoic acid, 1-methyl-2-naphthoic acid and 2-isopropyl-1-naphthoic acid.

55. Polycondensate according to one of Embodiments 46 to 54, in which the aromatic monocarboxylic acid, or the mixture of the acids, represents 20% to 52% by weight, or even 22% to 52% by weight and better still 25% to 50% by weight relative to the total weight of the polycondensate.

56. Polycondensate according to one of Embodiments 46 to 55, in which the polycarboxylic acid is chosen from linear, branched and/or cyclic, saturated or unsaturated, or even aromatic, polycarboxylic acids containing 2 to 20 carbon atoms, especially 3 to 18 and better still 4 to 12 carbon atoms, or even 4 to 10 carbon atoms; the acid comprising at least two carboxylic groups COOH and preferably from 2 to 4 COOH groups.

57. Polycondensate according to one of Embodiments 46 to 55, in which the cyclic anhydride corresponds to one of the following formulae:

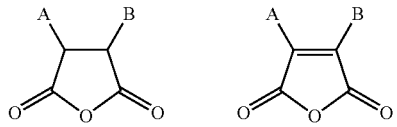

in which the groups A and B are, independently of each other:
- a hydrogen atom,
- a saturated or unsaturated, linear, branched and/or cyclic aliphatic, or alternatively aromatic, carbon-based radical; containing 1 to 16 carbon atoms, especially 2 to 10 carbon atoms or even 4 to 8 carbon atoms, especially methyl or ethyl;
- or alternatively A and B, taken together, form a saturated or unsaturated, or even aromatic, ring containing in total 5 to 7 and especially 6 carbon atoms.

58. Polycondensate according to one of Embodiments 46 to 57, in which the polycarboxylic acid, or the anhydride thereof, is chosen, alone or as a mixture, from:
- dicarboxylic acids such as decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid or maleic acid;
- tricarboxylic acids such as cyclohexanetricarboxylic acid, trimellitic acid, 1,2,3-benzenetricarboxylic acid or 1,3,5-benzenetricarboxylic acid;
- tetracarboxylic acids such as butanetetracarboxylic acid and pyromellitic acid;
- cyclic anhydrides of these acids and especially phthalic anhydride, trimellitic anhydride, maleic anhydride and succinic anhydride.

59. Polycondensate according to one of Embodiments 46 to 58, in which the polycarboxylic acid and/or the cyclic anhydride thereof represents 11% to 22% by weight and better still 12% to 20% by weight relative to the total weight of the polycondensate.

60. Polycondensate according to one of Embodiments 46 to 59, in which the polycondensate also comprises at least one silicone containing hydroxyl (OH) and/or carboxylic (COOH) functions.

61. Polycondensate according to one of Embodiments 46 to 60, in which the silicone is of the formula:

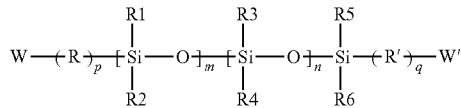

in which:
- W and W' are, independently of each other, OH or COOH; preferably, W=W';
- p and q are, independently of each other equal to 0 or 1;
- R and R' are, independently of each other, a saturated or unsaturated, or even aromatic, linear, branched and/or cyclic carbon-based and especially hydrocarbon-based divalent radical; containing 1 to 12 carbon atoms and especially 2 to 8 carbon atoms, and optionally also comprising one or more heteroatoms chosen from O, S and N, especially 0 (ether);
- R and/or R' may especially be of formula $-(CH_2)_a-$ with a=1-12, and especially methylene, ethylene, propylene or phenylene;
- or alternatively of formula $-[(CH_2)_xO]_z-$ with x=1, 2 or 3 and z=1-10; in particular x=2 or 3 and z=1-4; and better still x=3 and z=1;
- R1 to R6 are, independently of each other, a linear, branched and/or cyclic, saturated or unsaturated, or even aromatic, carbon-based radical containing 1 to 20 carbon atoms and especially 2 to 12 carbon atoms; preferably, R1 to R6 are saturated or aromatic, and may be chosen especially from alkyl radicals, in particular methyl, ethyl, propyl, isopropyl, butyl, pentyl, hexyl, octyl, decyl, dodecyl and octadecyl radicals, cycloalkyl radicals, in particular the cyclohexyl radical, aryl radicals, especially phenyl and naphthyl, arylalkyl radicals, especially benzyl and phenylethyl, and also tolyl and xylyl radicals;
- m and n are, independently of each other, integers between 1 and 140, and are such that the weight-average molecular mass (Mw) of the silicone is between 300 and 20 000, especially between 400 and 10 000 or even between 800 and 4000.

62. Polycondensate according to either of Embodiments 60 and 61, in which the silicone is chosen, alone or as a mixture, from α,ω-diol or α,ω-dicarboxylic polyalkylsiloxanes and especially α,ω-diol polydimethylsiloxanes and α,ω-dicarboxylic polydimethylsiloxanes; α,ω-diol or α,ω-dicarboxylic polyarylsiloxanes and especially α,ω-diol or α,ω-dicarboxylic polyphenylsiloxanes; polyarylsiloxanes containing silanol functions such as polyphenylsiloxane; polyalkylsiloxanes containing silanol functions such as polydimethylsiloxane; polyaryl/alkylsiloxanes containing silanol functions such as polyphenyl/methylsiloxane or polyphenyl/propylsiloxane.

63. Polycondensate according to one of Embodiments 60 to 62, in which the silicone represents 0.1% to 15% by weight, especially 1% to 10% by weight or even 2% to 8% by weight relative to the total weight of the polycondensate.

64. Process for preparing polycondensates according to one of Embodiments 46 to 63, which consists in:
- mixing the polyol and the aromatic and non-aromatic monocarboxylic acids,
- heating the mixture under an inert atmosphere, first to the melting point (generally 100-130° C.), and then to a temperature of between 150 and 220° C. until the monocarboxylic acids have been totally consumed, then
- optionally cooling the mixture to a temperature of between 90 and 150° C.,
- adding the polycarboxylic acid and/or the cyclic anhydride, and optionally the silicone containing hydroxyl or carboxylic functions, and then
- heating again to a temperature of less than or equal to 220° C.

65. Process according to Embodiment 64, in which one or more antioxidants are added to the reaction medium, especially in a weight concentration of between 0.01% and 1% relative to the total weight of monomers.

66. Process according to Embodiment 65, in which the antioxidant is chosen from BHT, BHA, TBHQ, 1,3,5-trimethyl-2,4,6-tris(3,5-di-tert-butyl-4-hydroxybenzyl)benzene, octadecyl 3,5-di-tert-butyl-4-hydroxycinnamate, methanetetrakis[methylene-3-(3,5-di-tert-butyl-4-hydroxyphenyl) propionate], octadecyl 3-(3,5-di-tert-butyl-4-hydroxyphenyl)propionate 2,5-di-tert-butylhydroquinone, 2,2-methylbis (4-methyl-6-tert-butyl-phenol), 2,2-methylenebis(4-ethyl-6-tert-butylphenol), 4,4-butylidenebis(6-tert-butyl-m-cresol), N,N-hexamethylenebis(3,5-di-tert-butyl-4-hydroxyhydrocinnamamide), pentaerythritoltetrakis(3-(3,5-di-tert-butyl-4-hydroxyphenyl)propionate); octadecyl 3-(3,5-di-tert-butyl-4-hydroxyphenyl)propionate, 1,3,5-tris(3,5-di-tert-butyl-4-hydroxybenzyl)-1,3,5-triazine-2,4,6-(1H,3H,5H)-trione; di(stearyl)pentaerythritol diphosphite, tris(2,4-di-tert-butylphenyl) phosphite; dilauryl thiodipropionate; bis(2,4-di-tert-butyl)pentaerythritol diphosphite; bis(2,4-bis)[2-phenyl-propan-2-yl]phenyl)pentaerythritol diphosphite, triphenyl phosphite, (2,4-di-tert-butylphenyl)pentaerythritol diphosphite; tris(nonylphenyl) phosphite; the 1:1 mixture of N,N-hexamethylenebis(3,5-di-tert-butyl-4-hydroxyhydrocinnamamide) and of tris(2,4-di-tert-butyl-phenyl) phosphate; tetrakis(2,4-di-tert-butylphenyl) phosphite; distearyl thiodipropionate; 2,4-bis(octylthiomethyl)-o-cresol; 4,6-bis (dodecylthiomethyl)-o-cresol.

As used herein, the phrases "selected from the group consisting of," "chosen from," and the like include mixtures of the specified materials. Terms such as "contain(s)" and the like as used herein are open terms meaning 'including at least' unless otherwise specifically noted.

All references, patents, applications, tests, standards, documents, publications, brochures, texts, articles, etc. mentioned herein are incorporated herein by reference. Where a numerical limit or range is stated, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

The invention claimed is:

1. A composition comprising, in a cosmetically or pharmaceutically acceptable medium, at least one polycondensate obtained by reacting:
   from 18% to 25% by weight, relative to a total weight of the polycondensate, of at least one polyol that is a saturated linear or branched hydrocarbon-based compound comprising 3 to 18 carbon atoms and 3 to 6 hydroxyl groups;
   from 10% to 35% by weight, relative to the total weight of the polycondensate, of at least one non-aromatic monocarboxylic acid given by the formula RCOOH, in which R is a saturated linear or branched hydrocarbon-based radical comprising 5 to 31 carbon atoms;
   from 25% to 50% by weight, relative to the total weight of the polycondensate, of at least one aromatic monocarboxylic acid selected from the group consisting of benzoic acid, o-toluic acid, m-toluic acid, p-toluic acid, 1-naphthoic acid, 2-naphthoic acid, 4-tert-butylbenzoic acid, 1-methyl-2-naphthoic acid, and 2-isopropyl-1-naphthoic acid; and
   from 12% to 20% by weight, relative to the total weight of the polycondensate, of at least one polycarboxylic acid anhydride of a polycarboxylic acid selected from the group consisting of decanedioic acid, dodecanedioic acid, cyclopropanedicarboxylic acid, cyclohexanedicarboxylic acid, cyclobutanedicarboxylic acid, naphthalene-1,4-dicarboxylic acid, naphthalene-2,3-dicarboxylic acid, naphthalene-2,6-dicarboxylic acid, suberic acid, oxalic acid, malonic acid, succinic acid, phthalic acid, terephthalic acid, isophthalic acid, pimelic acid, sebacic acid, azelaic acid, glutaric acid, adipic acid, fumaric acid, maleic acid, cyclohexanetricarboxylic acid, trimellitic acid, 1,2,3-benzenetricarboxylic acid, 1,3,5-benzenetricarboxylic acid, butanetetracarboxylic acid, pyromellitic acid, phthalic anhydride, trimellitic anhydride, maleic anhydride, and succinic anhydride.

2. The composition according to claim 1, wherein the polyol comprises 3 to 4 hydroxyl groups.

3. The composition according to claim 1, wherein the polyol comprises one or more oxygen atoms intercalated in the chain.

4. The composition according to claim 1, wherein the polyol comprises at least one member selected from the group consisting of:
   1,2,6-hexanetriol, trimethylolethane, trimethylolpropane, glycerol, pentaerythritol, erythritol, diglycerol, ditrimethylolpropane, xylitol, sorbitol, mannitol dipentaerythritol and triglycerol.

5. The composition according to claim 1, wherein the polyol comprises at least one member selected from the group consisting of glycerol, pentaerythritol and sorbitol.

6. The composition according to claim 1, wherein the non-aromatic monocarboxylic acid comprises at least one member selected from the group consisting of:
   caproic acid, caprylic acid, isoheptanoic acid, 4-ethylpentanoic acid, 2-ethylhexanoic acid, 4,5-dimethylhexanoic acid, 2-heptylhexanoic acid, 3,5,5-trimethylhexanoic acid, octanoic acid, isooctanoic acid, nonanoic acid, decanoic acid, isononanoic acid, lauric acid, tridecanoic acid, myristic acid, palmitic acid, stearic acid, isostearic acid, arachidic acid, behenic acid, cerotic acid (hexacosanoic acid); cyclopentanecarboxylic acid, cyclopentaneacetic acid, 3-cyclopentylpropionic acid, cyclohexanecarboxylic acid, cyclohexylacetic acid, and 4-cyclohexylbutyric acid.

7. The composition according to claim 1, wherein the non-aromatic monocarboxylic acid comprises at least one member selected from the group consisting of 2-ethylhexanoic acid, isooctanoic acid, lauric acid, palmitic acid and isostearic acid.

8. The composition according to claim 1, wherein the aromatic monocarboxylic acid comprises at least one member selected from the group consisting of benzoic acid, o-toluic acid, m-toluic acid and 1-naphthoic acid.

9. A process for treating a keratin material, comprising applying the composition as defined in claim 1 to the keratin material.

10. The process according to claim 9, wherein the keratin material is a finger nail.

* * * * *